(12) United States Patent
Wang et al.

(10) Patent No.: US 7,155,285 B2
(45) Date of Patent: Dec. 26, 2006

(54) APPARATUS FOR INDUCING ENERGIES OF ALPHA RHYTHM TO THE HUMAN BODY

(76) Inventors: Xiaoming Wang, 27 Calle Alamitos, Rancho Santa Margarita, CA (US) 92688; Huijian Zou, 228 Longcheng Industrial Park, Shenzhen, Guangdong (CN) 518172; Wei Chen, 27 Calle Alamitos, Rancho Santa Margarita, CA (US) 92688

( * ) Notice: Subject to any disclaimer, the term of this patent is extended or adjusted under 35 U.S.C. 154(b) by 360 days.

(21) Appl. No.: 10/733,139

(22) Filed: Dec. 11, 2003

(65) Prior Publication Data
US 2004/0143296 A1    Jul. 22, 2004

Related U.S. Application Data

(60) Provisional application No. 60/434,201, filed on Dec. 17, 2002.

(51) Int. Cl.
*A61N 1/18*    (2006.01)
(52) U.S. Cl. .................. 607/45; 607/39; 607/40; 600/26
(58) Field of Classification Search ............ 607/2, 607/45–46, 50, 65, 39–40; 600/545, 26
See application file for complete search history.

(56) References Cited

U.S. PATENT DOCUMENTS

| | | | | |
|---|---|---|---|---|
| 3,762,396 A * | 10/1973 | Ballentine et al. | ............ | 600/26 |
| 4,227,516 A * | 10/1980 | Meland et al. | ................ | 600/26 |
| 5,289,438 A * | 2/1994 | Gall | .............................. | 369/4 |
| 5,356,368 A * | 10/1994 | Monroe | ....................... | 600/28 |
| 5,691,325 A * | 11/1997 | Sandyk | ....................... | 514/159 |
| 5,954,629 A * | 9/1999 | Yanagidaira et al. | ......... | 600/27 |
| RE36,348 E * | 10/1999 | Carter et al. | ................ | 600/545 |
| 6,622,036 B1* | 9/2003 | Suffin | ......................... | 600/544 |
| 2001/0003145 A1* | 6/2001 | Mori et al. | ................. | 600/544 |

* cited by examiner

*Primary Examiner*—Jeffrey R. Jastrzab

(57) ABSTRACT

Alpha rhythm brain waves are related to mental and physical relaxation and healing. Based on the studies of bionics, this invention relates to inducing oscillatory alpha rhythm to the human body, and relates to the means of the alpha rhythm machine applied to human body. Research of the alpha rhythm of human brain wave patterns and EEG has indicated special recorded data of alpha rhythm brain waveform which is the bearing of the proper biological information of relaxing and healing. The apparatus was developed and built to construct and release the simulated human brain alpha rhythm signals which are at the frequencies ranging 8 Hz–14 Hz and at the amplitudes altered in high or low. Both the frequencies and the amplitudes are changing at a non-stationary random order in the duration of the event, respectively. The electrical signals are transformed via a transducer, into three forms of energy, 1, alpha rhythm electromagnetic energy and alpha rhythm interfering static magnetic energy; 2, alpha rhythm sub-audio acoustic oscillatory energy; and 3, alpha rhythm mechanical vibrational energy. The combining energies from the apparatus can benefit the whole human body or only the area affected by illness, for example, treating men's prostate problems or treating sleep disorders.

11 Claims, 8 Drawing Sheets

FIG. 5A
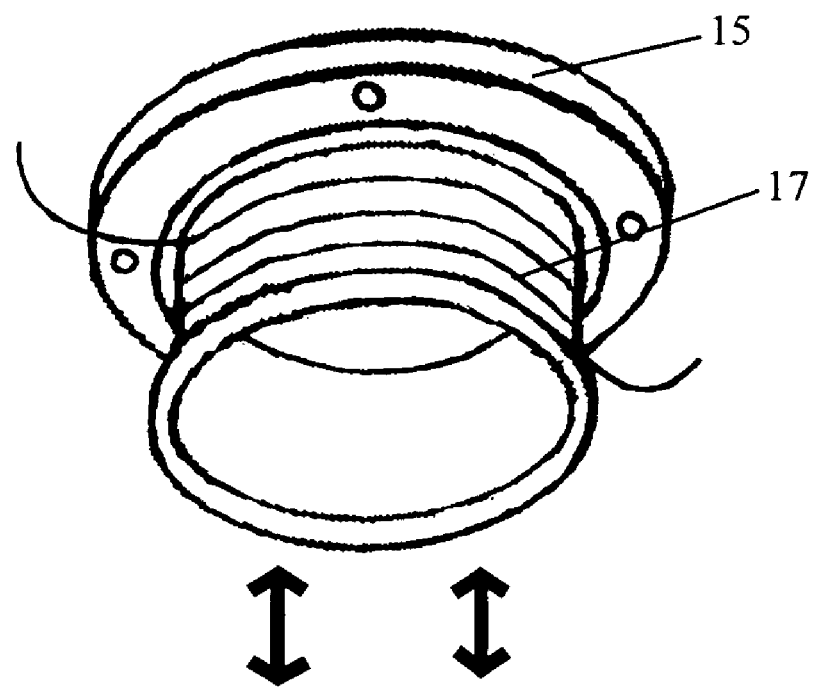
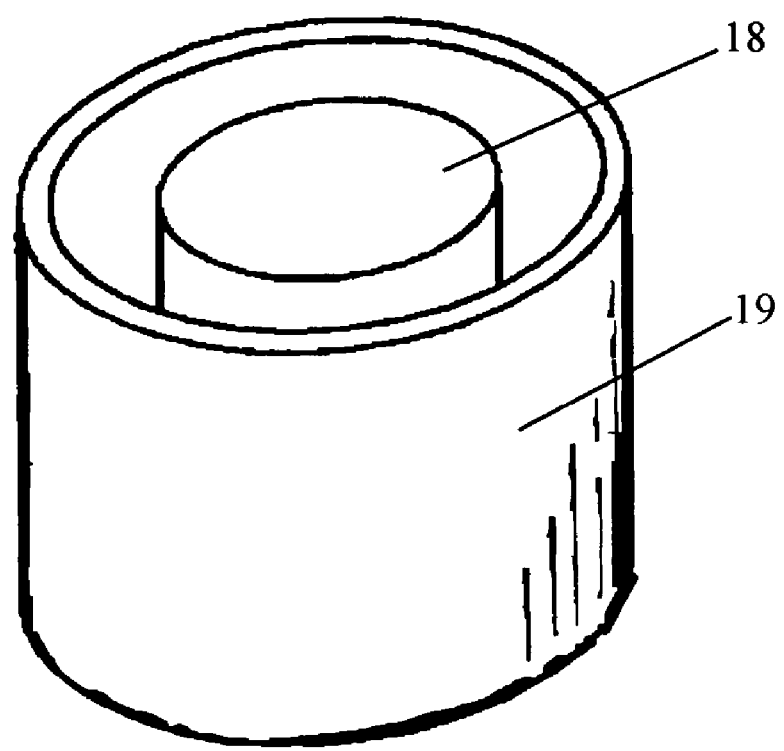
FIG. 5B

APPARATUS FOR INDUCING ENERGIES OF ALPHA RHYTHM TO THE HUMAN BODY

RELATED APPLICATIONS

U.S. Pat. D469543S, filed May 2003, Wang, D24/215, is a design patent for the present invention.

This application claims the benefit of U.S. Provisional Patent Application No. 60/434,201, filed on Dec. 17, 2002.

FEDERALLY SPONSORED RESEARCH

Not applicable

FIELD OF INVENTION

This invention relates to inducing oscillatory alpha rhythm to the human body, and relates to the means of the alpha rhythm machine applied to the body accordingly, for example, treating men's prostate problems or sleep disorders.

BACKGROUND OF THE INVENTION

As the growing science of bionics, it has been known that alpha rhythm brain waves are related to mental and physical relaxation and healing.

When neurons in the human brain are active, their electrical activity is measured in brain waveforms via Electroencephalogram (EEG). The EEG patterns are correlated with changes in human mental and physical functions. Based on the frequencies of brain waveforms recorded from the EEG, there are four rhythm patterns, Delta, Theta, Alpha and Beta. Alpha rhythm is the frequency range between 8–14 Hz. Medical studies have shown that alpha rhythm is associated with tranquil state of consciousness, meditation, the mind/body integration and with physical relaxation and healing. Research of bionics has suggested that induction of alpha rhythm might affect our mind and body.

Several types of apparatus generating different frequencies via different means have been proposed. In U.S. Pat. No. 4,834,701 (1989), frequency reduction in human brain wave is inducible by allowing the human brain to perceive 4–16 Hz beat sound and an apparatus induces a low frequency beat sound at 14–16 Hz. These beat sounds are released via earphone or loudspeaker. In U.S. Pat. No. 5,113,852 (1992), an audio frequency in the range from 20 Hz to 200 Hz is applied to produce a pleasant feeling for the body relaxation. In U.S. Pat. No. 5,289,438 (1994), it involves the simultaneous application of multiple sound stimuli at different frequencies and waveforms. In U.S. Pat. No. 6,017,302 (2000), ½ Hz and 2.5 Hz resonances are generated, and the apparatus consists of a portable battery powered source of weak sub-audio acoustic radiation. In U.S. Pat. No. 6,461,316 (2002), a chaos signal generator is added into a therapeutic massager for the purpose of increased therapeutic effectiveness.

In U.S. Pat. No. 4,002,164 (1977), the prostate massager is used for massaging and treating an inflammatory prostate gland. However, it utilizes a massaging head inserted into the rectum, which is inconvenient to use.

In Chinese patent 8510062 (1985), the device generates a spectrum of signals at a range of 0–250 Hz. In Chinese patent 95224307.5 (1995), the device generates a spectrum of signals at a range of 0–30 Hz. Both devices above are based on the studies of traditional Chinese medicine and Qi Gong (or Chi Kung), in which vibrational signals are emitted from Qi Gong masters or healers. In their electrical circuits, transistors are used, as the oscillatory sources to generate noise signals. In their electrical acoustic transducers, in which the mechanical forces result from magnetic reaction, each consists of a large, heavy conductor that is limited to movement and causes efficiency reduction and amplitude distortion. Furthermore, there is a metal house that blocks the radiating force of the magnet inside the transducer.

Several magnetic devices have been proposed. In U.S. Pat. No. 5,235,967 (1993), the electromagnetic impact massager is in the form of a therapeutic garment. Drive coils are mounted within the compartments adjacent to the conductive elements and produce a pulsed electromagnetic field. In U.S. Pat. No. 5,312,321 (1994), the static magnetic device is comprised of four magnetic bodies, which can suppress neuron action potential firings. In U.S. Pat. No. 5,707,333 (1998), the combined multiple static magnetic flux can reduce the transmission in a human body of sensation from a body part to the brain. The north pole of the static magnet is directed toward the body part. In U.S. Pat. No. 6,023,116 (2000), it involves an electromagnetic vibration at different frequencies to generate a rotary direction.

In U.S. Pat. No. 6,553,254 (2003), it utilizes a method of combining two energy-facilitating units for a therapeutic purpose, the first being a non-living-source physical energy and the second being a living-source chemical energy.

The present invention pertains to the mechanism of bionics by applying the simulated alpha rhythm of human brain waveforms. After selectively obtaining a recording of alpha rhythm brain waves, which is the bearing of the proper biological information of relaxing and healing, the apparatus is developed to construct and release the simulated brain alpha rhythm which is transformed into three forms of energies: 1, alpha rhythm electromagnetic energy and alpha rhythm interfering static magnetic energy; 2, alpha rhythm sub-audio acoustic energy and 3, alpha rhythm mechanical vibrational energy.

SUMMARY OF THE INVENTION

The present invention is like a bionics machine selectively inducing brain alpha rhythm, i.e., the alpha rhythm machine. It employs special recorded data of simulated brain alpha rhythm. An electrical integrated system constructs the signals to mimic this brain alpha rhythm. A transducer transforms the signals into the alpha rhythm electromagnetic energy, along with alpha rhythm interfered static magnetic energy and alpha rhythm sub-audio acoustic energy and low frequency mechanical vibrational energy. The combining alpha rhythm energies can affect the body for relaxing and healing. The apparatus can be applied to different conditions and parts of the body, such as treatment of prostate problems or treatment of sleep disorders.

The apparatus according to the present invention have the following features:

1. to provide special recorded data of simulated brain alpha rhythm which bears biological information of relaxing and healing;
2. to provide special recorded data of simulated brain alpha rhythm at a range of peak frequencies 8–14 Hz;
3. to provide special recorded data of simulated brain alpha rhythm at a range of different amplitudes;
4. to provide special recorded data of simulated brain alpha rhythm at non-stationary random order during the oscillatory motion event;
5. to provide an electrical digital system generating signals to mimic this brain alpha rhythm;

6. to provide a transducer in which the signals are transformed into an alpha rhythm electromagnetic energy;
7. to provide a transducer in which a static magnet generates a radiating energy, but interfered by the alpha rhythm electromagnetic field;
8. to provide a transducer in which the signals are transformed into a sub-audio acoustic energy; and
9. to provide a transducer generating the alpha rhythm mechanical vibrational energy.

The above features of the apparatus of the present invention make it possible to provide further objects and advantages:

1. Because of the combining energies of the electromagnetic energy, interfered static magnetic energy, sub-audio acoustic energy and mechanical vibrational energy, the effects in relaxing and healing are much stronger than either of them used alone.
2. Some of the combining energies, like electromagnetic energy and sub-audio acoustic energy, can travel far in distance and can reach deep tissue and organs, and can be applied to the whole body or only to the area affected by illness.
3. The apparatus is easy and safe to use and it can be applied directly to skin or through clothes.

BRIEF DESCRIPTION OF THE DRAWINGS

FIGS. 5A and 5B are a perspective view of the conductor and a perspective view of the static magnet, respectively.

DETAILED DESCRIPTION OF THE PREFERRED EMBODIMENTS

Figure 1:
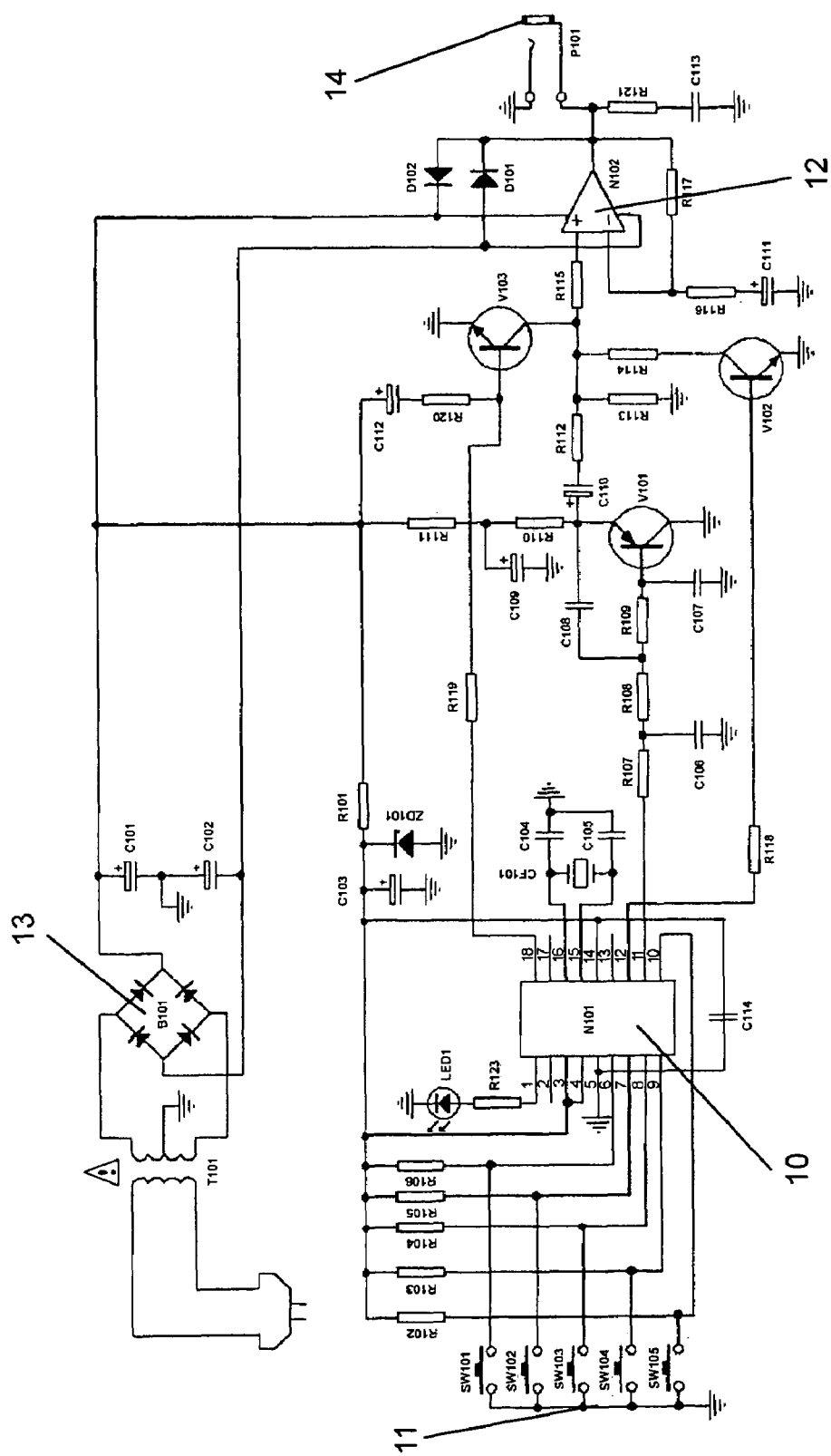
FIG. 1 is a schematic circuit diagram of a logic board embodying the present invention.

FIG. 1 shows the schematic circuit. A specified chip CPU (N101) 10 is to control all the functions. There are a built-in D/A converter, a controller for timing and a controller for the output of current amplitude. The keys 11 of SW101, SW102, SW103, SW104 and SW105 correspond to the functions of "20" minutes; "low" in current amplitude; "10" minutes; ON/OFF in power and "high" in current amplitude, respectively. The integrated circuit chip 10 is the source of oscillatory signals controlled in composition with the crystal CF 101 (4.0 M) to pin 15 and pin 16 for the source of timing. A controller of timing is built with "10" minutes to pin 6 and "20" minutes to pin 8.

A power controller is built in which the output from pin 18 is sent to a transistor V103, along with the power switch (pin 9)(ON/OFF).

A controller of current amplitudes is built in which outputs from pin 7 and pin 10 are sent to pin 12 for altering the current amplitude, along with resistors R112 (22 K), R113 (10 K), R114 (6.8 K), and transistor V102.

The signals from pin 11 are filtered via three steps of low-pass system (the Protel Simulation). The first step is by resistors R107 (150 K), R108 (150 K) and R109 (220K); the second step is by capacitors C106 (15 n), C107 (15 n) and C108 (100 n) and the third step is by transistor (V101).

The filtered signals are amplified via integrated circuit (N102) 12, in accordance with the ratio of resistors R116 (1 K) and R117 (33 K) and the AC feedback circuit consisting of resistor R116 (1 K) and capacitor C111 (10μ).

The amplifying circuit (N 102) 12 is altered by the bridge-rectifier circuit B 101 13, along with capacitors C101 (3300μ) and C102 (3300μ).

The altered signals are reduced by the ratio value of resistors R112 (22 K) and R113 (10 K). The load impedance of the circuit is controlled by resistor R121 and capacitor C113 (22μ).

A voltage stabilized circuit consists of VR-tube ZD 101 (5.1 V), along with capacitor C103 (100μ) and resistor R101 (1 K). The delayed circuit consists of capacitor C112 (10μ) and resistor R120 (100 K) for noise reduction. The diodes D101 and D102 are used to protect the circuits.

The signals, or current, from the electrical system are released 14 to the transducer.

Figure 2A:
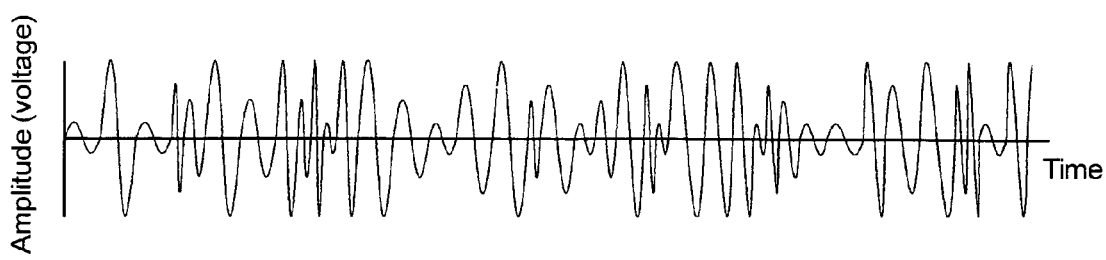
FIG. 2 illustrates a recording trace of the simulated brain alpha rhythm.
Figure 2B:
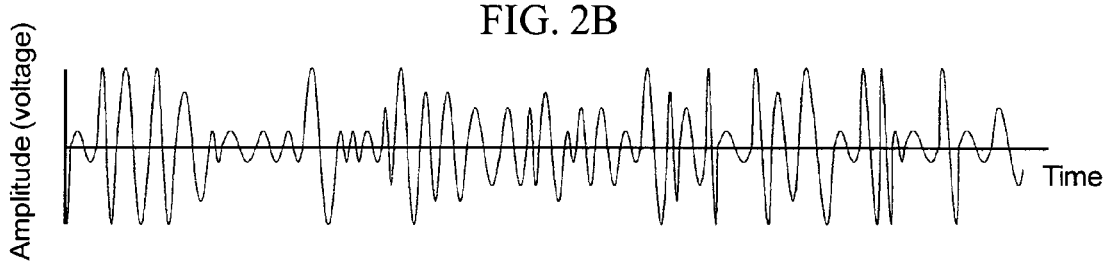
Figure 2C:
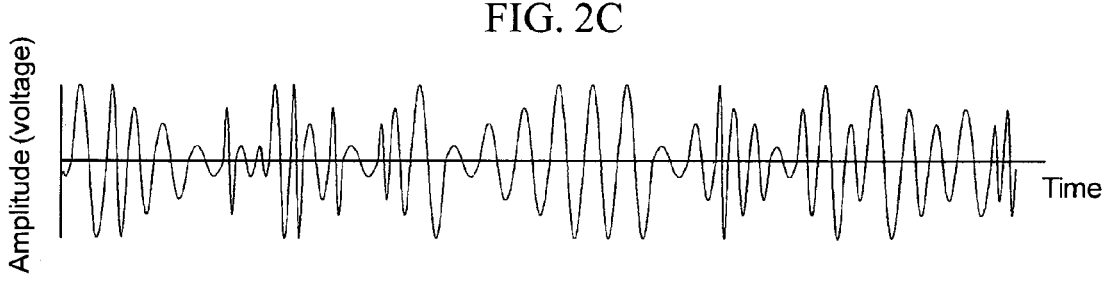

FIG. 2 shows the recorded data of simulated alpha rhythm waveforms. These waveform traces, 2A, 2B and 2C, are consecutive from a single recording of 12 seconds. The frequencies are set to mimic the human alpha rhythm waveforms at an average range of 8–14 Hz. The amplitudes can either increase or decrease. Both the frequencies and the amplitudes are changing at a non-stationary random order in the duration of the motion event. The amplitude may alternatively be defined by the voltage, which is related directly to the conditions and parts of the body.

Figure 3A:
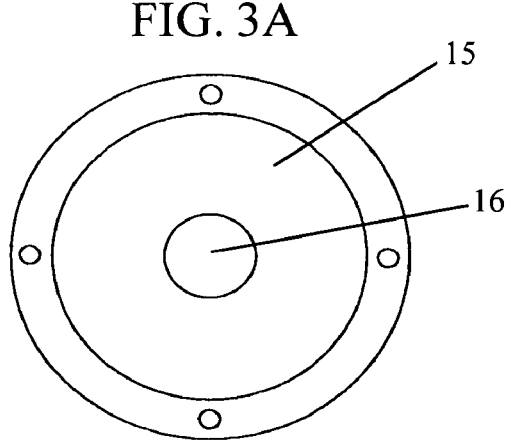
FIGS. 3A, 3B, and 3C are the top view of the conductor; a sectional view of the conductor and a perspective view of the conductor with which the wire is coiled, respectively.
Figure 3B:
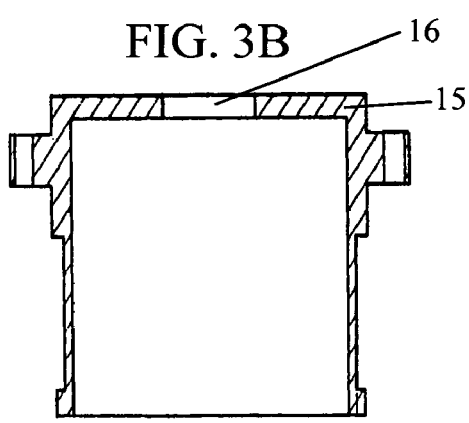
Figure 3C:
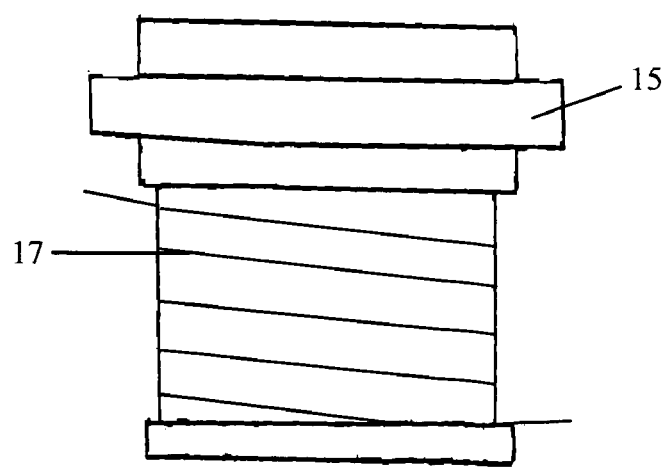

FIG. 3 illustrates the conductor as the center element of the transducer. There is a circle hole 16 through the top of the conductor 15. A wire is coiled 17 with the conductor. When the current is turned on, the coil generates the electromagnetic energy. Based on the motion of alpha rhythm with alternative frequencies of 8–14 Hz and the alternative amplitudes, the current in the transducer is defined as the alternative current, and electromagnetic field is defined as the alternative electromagnetic field. The conductor 15 attaches to a diaphragm previously known.

Figure 4A:
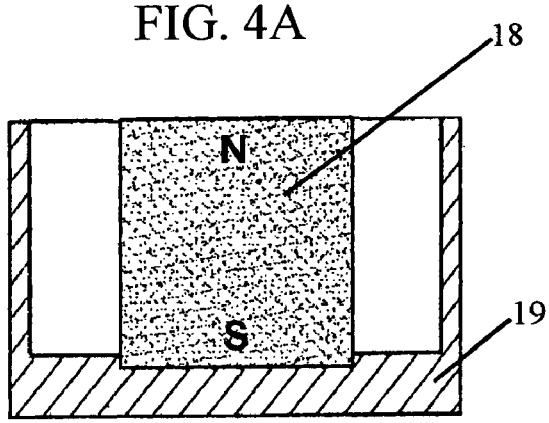
FIGS. 4A, 4B and 4C are a sectional view of the static magnet and the casing; a top view of the static magnet and the casing and a perspective view of the static magnet with the north (N) pole exposed to the outside and the casing, respectively.
Figure 4B:
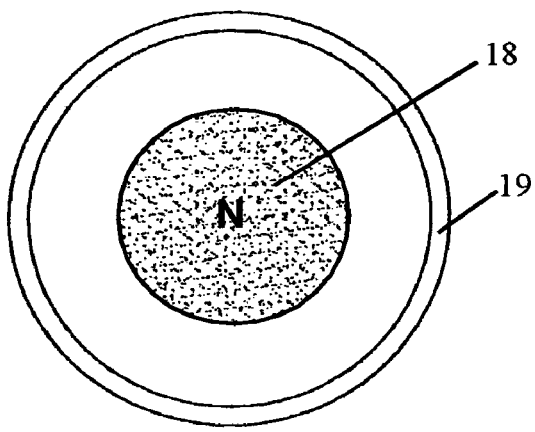
Figure 4C:
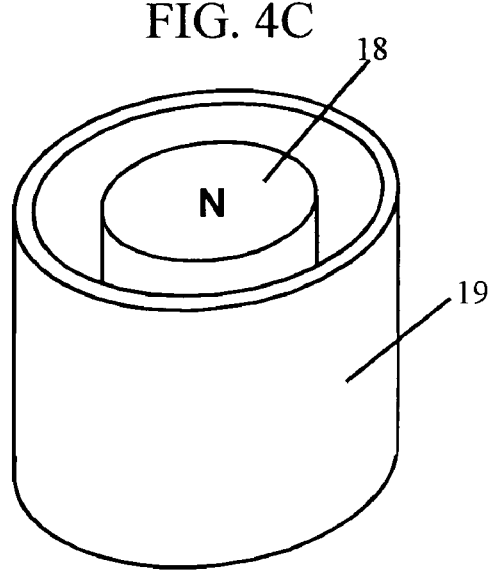

FIG. 4 illustrates the static magnet and the casing of the transducer. The static magnet 18 is embedded in the center of the casing 19. The north (N) pole of the static magnet is free towards the outside, and the south (S) pole of the static magnet is connected to the casing. The north (N) pole of the static magnet is pointing to the human body. The energy of the static magnet is interfered by the alternative electromagnetic field according to the alpha rhythm.

FIG. 5 illustrates the functional relationship between the conductor 15 and magnet 18 of the transducer. When the current is on and the current flows in the wire coiled 17, the electromagnetic field is activated and the electromagnetic energy is radiated. The electromagnetic field can interfere the static magnetic field. Radiating energy of the interfered static magnet 18 in the casing 19 can transmit through the circle hole 16 of the conductor 15 to the human body directly.

The two forces of electromagnetic field and static magnetic field cause the motion of the diaphragm which is the radiating source of the sub-audio acoustic energy. Furthermore, the two forces of electromagnetic field and static magnetic field enable the conductor 15 to move in the direction of up or down, accordingly. The movement of the conductor 15 generates the mechanical vibrational energy of the transducer.

Figure 6:
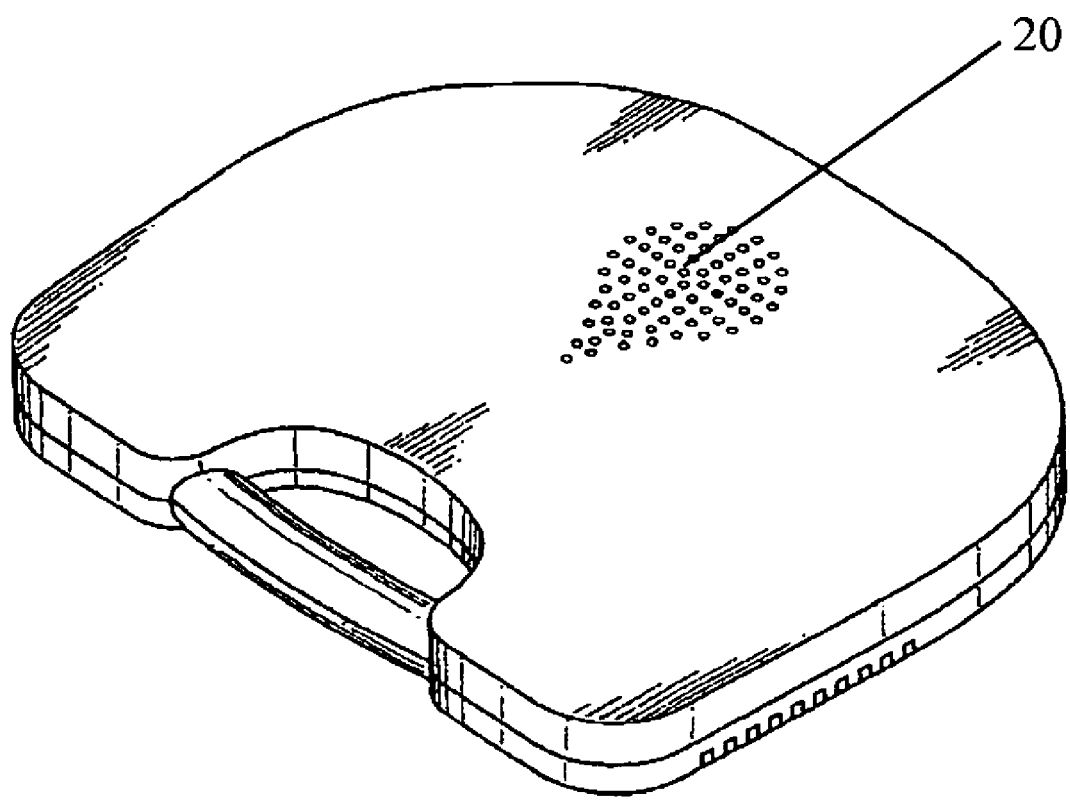
FIG. 6 illustrates a perspective view of the apparatus embodying the present invention.

FIG. 6 shows the apparatus in which the electrical elements and transducer are built. The transducer is located under the small multi-holes 20, through which the combining alpha rhythm energies of the present invention are centered and released. The apparatus is light in weight and easy to carry. The ornamental design for the apparatus has been patented by U.S. patent and trademark office, U.S. D469,543 S, January, 2003.

Figure 7:
FIG. 7 illustrates an application of the present invention in the treatment of prostate problems.

FIG. 7 illustrates an example of the application of present invention for treatment of men's prostate problems. The apparatus 21 is placed in a sitting position. The apparatus 21 can be used for treating men's prostate problems, particularly in chronic conditions. The high amplitude (voltage) or strong intensity and the frequency at a range of 9–11 Hz are selected The position of the treatment is to sit on the apparatus 21 and place holes 20 of the transducer close to the perineum with the clothing on or off. Treatment should be conducted 2 times a day, 20–30 minutes a time, for a course of 20–30 days.

Clinical improvements of the conditions are evident after 1–2 courses of application. The symptoms are relieved significantly, including difficulty of urination, pain and burning sensation on urination, frequency and urgency of urination, passing only small amounts of urine, and lower back and abdominal pain. Studies have shown that thirty patients being treated experienced an effective rate higher than 90%.

Figure 8:
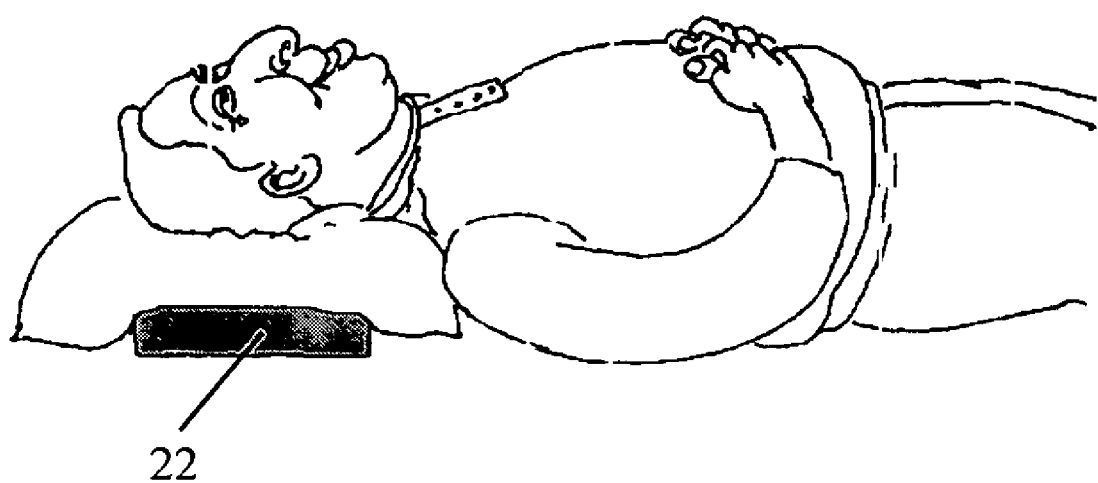
FIG. 8 illustrates an application of the present invention in the treatment of sleep disorders.

FIG. 8 illustrates an example of application of the present invention for the treatment of sleep disorders.

The apparatus 22 can be used to treat sleep disorders, such as long-term insomnia caused by general anxiety, stress, depression or other conditions. The low amplitude (voltage) or weak intensity and the frequency at a range of 8–12 Hz are selected.

The position of the treatment is to place the apparatus 22 under a pillow when sleeping. Treatment should be conducted at bedtime for 30–60 minutes, for a course of 30–40 days.

The apparatus of the present invention will relax the body, reduce anxiety and stress, detach awareness, provide a bridge between the conscious and subconscious mind, and induce sleep and dream states.

We claim:

1. An apparatus for inducing energies of alpha rhythm to the human body, comprising:
    (a) means for creating a signal of simulated brain alpha rhythm with an average frequency range of 8–14 Hz at a random order, and a changing of an amplitude during a recording, and
    (b) means for inducing energies of alpha rhythm, comprising:
        an electromagnetic energy with said signal of simulated brain alpha rhythm, an interfered static magnetic energy with said signal of simulated brain alpha rhythm, a sub-audio acoustic energy with said signal of simulated brain alpha rhythm and a mechanical vibrational energy with said signal of simulated brain alpha rhythm.

2. The apparatus according to claim 1, wherein an integrated circuit is programmed logically and intelligently for said signal of simulated brain alpha rhythm.

3. The apparatus according to claim 1, wherein an integrated circuit generates said signal of simulated brain alpha rhythm.

4. The apparatus according to claim 1, wherein a circuit controls the amplitude of said signal of simulated brain alpha rhythm.

5. The apparatus according to claim 1, wherein a circuit filters said signal of simulated brain alpha rhythm.

6. The apparatus according to claim 1, wherein an integrated circuit amplifies said signal of simulated brain alpha rhythm.

7. The apparatus according to claim 1, further comprising a transducer containing means for transforming said signal of simulated brain alpha rhythm into said energies of alpha rhythm, comprising: said electromagnetic energy with said signal of simulated brain alpha rhythm, said interfered static magnetic energy with said signal of simulated brain alpha rhythm, said sub-audio acoustic energy with said signal of simulated brain alpha rhythm and said mechanical vibrational energy with said signal of simulated brain alpha rhythm.

8. The transducer according to claim 7, wherein a conductor is centered inside said transducer.

9. The transducer according to claim 8, wherein a static magnet is positioned under said conductor for moving said conductor, with a north (N) pole adapted to confront the human body and a south (S) pole mounted to a casing.

10. A method of treating men's prostate problems comprising a step of a user sitting on the apparatus of claim 1 for inducing said energies of alpha rhythm, comprising: said electromagnetic energy with said signal of simulated brain alpha rhythm, said interfered static magnetic energy with said signal of simulated brain alpha rhythm, said sub-audio acoustic energy with said signal of simulated brain alpha rhythm and said mechanical vibrational energy with said signal of simulated brain alpha rhythm.

11. A method of treating sleep disorder comprising a step of a user lying on a pillow on top of the apparatus of claim 1 for inducing said energies of alpha rhythm, comprising: said electromagnetic energy with said signal of simulated brain alpha rhythm, said interfered static magnetic energy with said signal of simulated brain alpha rhythm, said sub-audio acoustic energy with said signal of simulated brain alpha rhythm and said mechanical vibrational energy with said signal of simulated brain alpha rhythm.

* * * * *

(12) EX PARTE REEXAMINATION CERTIFICATE (6496th)
United States Patent
Wang et al.

(10) Number: US 7,155,285 C1
(45) Certificate Issued: Oct. 28, 2008

(54) APPARATUS FOR INDUCING ENERGIES OF ALPHA RHYTHM TO THE HUMAN BODY

(76) Inventors: Xiaoming Wang, 27 Calle Alamitos, Rancho Santa Margarita, CA (US) 92688; Huijan Zou, 228 Longcheng Industrial Park, Shenzhen, Guangdong (CN), 518172; Wei Chen, 27 Calle Alamitos, Rancho Santa Margarita, CA (US) 92688

Reexamination Request:
No. 90/008,505, Mar. 12, 2007

Reexamination Certificate for:
Patent No.: 7,155,285
Issued: Dec. 26, 2006
Appl. No.: 10/733,139
Filed: Dec. 11, 2003

Related U.S. Application Data

(60) Provisional application No. 60/434,201, filed on Dec. 17, 2002.

(51) Int. Cl.
*A61N 1/18* (2006.01)

(52) U.S. Cl. .............................. 607/45; 607/39; 607/40; 600/26

(58) Field of Classification Search ................ None
See application file for complete search history.

(56) References Cited

U.S. PATENT DOCUMENTS 6,461,316 B1 10/2002 Lee et al.
7,155,285 B2 12/2006 Wang et al.

FOREIGN PATENT DOCUMENTS

| CN | 85 1 00622 | 7/1986 |
| CN | 85100622 | 5/1988 |
| CN | 95224307.5 | 7/1996 |

OTHER PUBLICATIONS

Richard Lee, Xiaoming Wang, The Use of Surface Electromyogram to Examine the Effects of the Infratonic QGM on Electrical Activity of Muscles. 1995.
Second Amened Complaint for (1) False Designation of Origin—Unfair Competition, (2) False Advertising et al. In US District Court, Mar. 10, 2003, 1st page.
Order for Summary Judgment, In US District Court, May 5, 2004.
Richard Lee, Xiaoming Wang, Release and Settlement Agreement, Jun. 28, 2004.
Joint Stipution and Order for Dismissal of All Claims by and Between China Healthways Institute, Inc. and East Health Development Group, Inc., In US District Court, Jul. 12, 2004.

(Continued)

*Primary Examiner*—Beverly M. Flanagan

(57) ABSTRACT

Alpha rhythm brain waves are related to mental and physical relaxation and healing. Based on the studies of bionics, this invention relates to inducing oscillatory alpha rhythm to the human body, and relates to the means of the alpha rhythm machine applied to human body. Research of the alpha rhythm of human brain wave patterns and EEG has indicated special recorded data of alpha rhythm brain waveform which is the bearing of the proper biological information of relaxing and healing. The apparatus was developed and built to construct and release the simulated human brain alpha rhythm signals which are at the frequencies ranging 8 Hz–14 Hz and at the amplitudes altered in high or low. Both the frequencies and the amplitudes are changing at a nonstationary random order in the duration of the event, respectively. The electrical signals are transformed via a transducer, into three forms of energy, 1, alpha rhythm electromagnetic energy and alpha rhythm interfering static magnetic energy; 2, alpha rhythm sub-audio acoustic oscillatory energy; and 3, alpha rhythm mechanical vibrational energy. The combining energies from the apparatus can benefit the whole human body or only the area affected by illness, for example, treating men's prostate problems or treating sleep disorders.

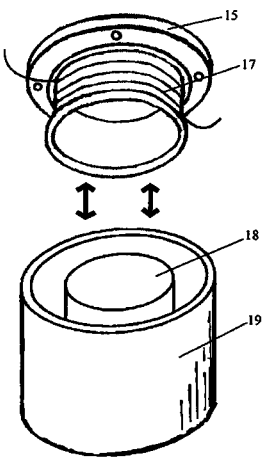

OTHER PUBLICATIONS

Opinion by Bucher, Administrative Trademrk Judge, USPTO, TTAB, Apr. 28, 2006.

A Comparison Study—The Infratonic QGM 4.3 From CHI Institute and The 54-888 from East Health. p. 6 Section 4

"Reversed Magnet in the 54-888" CHI Institute Aug. 15, 2003, 20,000 Printed in Santa Ana, CA by Kenny the Printer.

Infratonic Theraphy Users Guide—p. 37 A1 Published by CHI Institute in 2002, printed by Whitehall Printing, Naples, FL.

EX PARTE REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–11 is confirmed.

* * * * *